United States Patent [19]
Lusky et al.

[11] Patent Number: 6,066,478
[45] Date of Patent: May 23, 2000

[54] HELPER VIRUSES FOR PREPARING RECOMBINANT VIRAL VECTORS

[75] Inventors: Monika Lusky, Freiburg, Germany; Majid Mehtali, Illkirch Graffenstaden, France

[73] Assignee: Transgene S.A., Strasbourg, France

[21] Appl. No.: 09/011,257

[22] PCT Filed: Jul. 30, 1996

[86] PCT No.: PCT/FR96/01200

§ 371 Date: Jan. 30, 1998

§ 102(e) Date: Jan. 30, 1988

[87] PCT Pub. No.: WO97/05255

PCT Pub. Date: Feb. 13, 1997

[30] Foreign Application Priority Data

Jul. 31, 1995 [FR] France .................................. 95 09289

[51] Int. Cl.[7] ........................ C12N 15/64; C12N 15/861; C12N 5/10; C07H 21/04
[52] U.S. Cl. .................. 435/91.41; 435/91.4; 435/91.42; 435/320.1; 435/455; 435/456; 435/457; 435/325; 435/366; 435/369; 536/23.2; 536/23.4; 536/23.5; 536/23.7
[58] Field of Search ................................ 435/320.1, 69.1, 435/455, 456, 457, 325, 366, 369, 235.1, 91.4, 91.41, 91.42; 424/93.2, 93.6; 536/23.2, 23.4, 23.7, 23.5

[56] References Cited

FOREIGN PATENT DOCUMENTS

| 0 300 422 | 1/1989 | European Pat. Off. . |
| 0 488 528 | 6/1992 | European Pat. Off. . |
| 2 707 664 | 1/1995 | France . |
| WO 96/40955 | 12/1996 | WIPO . |

OTHER PUBLICATIONS

Gage et al., J. Virol., vol. 66, No. 9, pp. 5509–5515, Sep. 1992.
W. French Anderson, Nature, vol. 392, pp. 25–30, Apr. 30,1998.
Ross et al., Human Gene Therapy, vol.7, pp.1781–1790, Sep. 1996.
Verma et al., Nature, vol. 389, pp. 239–242, Sep. 18, 1997.
Orkin et al., "Report and Recommendations of the Panel to Assess the NIH Investment in Research on Gene Therapy", Dec. 7, 1995.
J. Mol. Biol. (1993), 230(1), 174–85 CODEN:J-MOBAK;ISSN: 0022-2836, XP000568383, Ayres, Elaine K. et al: "Precise deletions inlarge bacterial genomes by vector–mediated excision (VEX). The trfa gene of promiscuous plasmid RK2 is essential for replication in several Gram–negative hosts".
Proc. Natl. Acad. Sci. U.S.A. (1987), 84 (24), 9108–12 CODEN: PNASA6;ISSN: 0027-8424, XP002002088, Sauer, Brian et al, "Site–specific insertion of DNA into a pseudorabies virus vector".
Nucleic Acids Res. (1989), 17(1), 147–61 CODEN: NARHAD; ISSN: 0305–1048, XP002002089, Sauer, Brian et al: "Cre–stimulated recombination at loxP — containing DNA sequences placed into the mammalian genome".

*Primary Examiner*—David Guzo
*Attorney, Agent, or Firm*—Burns, Doane, Swecker & Mathis, L.L.P.

[57] ABSTRACT

Novel helper vectors are provided for complementing defective recombinant viral vectors, characterized in that they are provided with recombination sequences recognized by a recombinase. A complementation cell expressing the recombinase, and a method for preparing recombinant viral vectors as infectious viral particles for transferring and expressing genes of interest in a host organism or cell, are also provided. The invention is particularly suitable for use in gene therapy, especially in humans.

24 Claims, 7 Drawing Sheets

FIG.1

FIG_2

FIG_3

FIG_6

FIG. 7

SEQUENCE LISTING

<160> NUMBER OF SEQ ID NOS: 5

<210> SEQ ID NO 1
<211> LENGTH: 34
<212> TYPE: DNA
<213> ORGANISM: Bacteriophage P1

<400> SEQUENCE: 1
ataacttcgt ataatgtatg ctatacgaag ttat                       34

<210> SEQ ID NO 2
<211> LENGTH: 34
<212> TYPE: DNA
<213> ORGANISM: Saccharomyces cerevisiae

<400> SEQUENCE: 2
gaagttccta tactttctag agaataggaa cttc                       34

<210> SEQ ID NO 3
<211> LENGTH: 31
<212> TYPE: DNA
<213> ORGANISM: Zygosaccharomyces rouxii

<400> SEQUENCE: 3
ttgatgaaag aatacgttat tctttcatca a                          31

<210> SEQ ID NO 4
<211> LENGTH: 45
<212> TYPE: DNA
<213> ORGANISM: synthetic oligonucleotide (loxP)

<400> SEQUENCE: 4
agctataact tcgtataatg tatgctatac gaagttatct cgaga           45

<210> SEQ ID NO 5
<211> LENGTH: 45
<212> TYPE: DNA
<213> ORGANISM: synthetic oligonucleotide (loxP)

<400> SEQUENCE: 5
agcttctcga gataacttcg tatagcatac attatacgaa gttat           45

HELPER VIRUSES FOR PREPARING RECOMBINANT VIRAL VECTORS

The present invention relates to novel helper vectors allowing defective recombinant viral vectors, which have the characteristic of being provided with recombination sequences recognized by a recombinase, to be complemented. It likewise relates to a complementation cell expressing the recombinase as well as a method of preparation of recombinant viral vectors in the form of infectious viral particles allowing the transfer and the expression of genes of interest in a cell or a host organism. The invention is of very particular interest for gene therapy prospects, especially in man.

The possibility of treating human diseases by gene therapy has passed in the course of a few years from the stage of theoretical considerations to that of clinical applications. The first protocol applied to man was initiated in the United States in September 1990 on a patient who was genetically immunodeficient because of a mutation affecting the gene coding for adenine deaminase (ADA). The relative success of this first experiment encouraged the development of new gene therapy protocols for various genetic or acquired diseases (infectious diseases and especially viral diseases such as AIDS or cancers). The great majority of the protocols described until now employ viral vectors to transfer and express the therapeutic gene in the cells to be treated.

Figure 1:
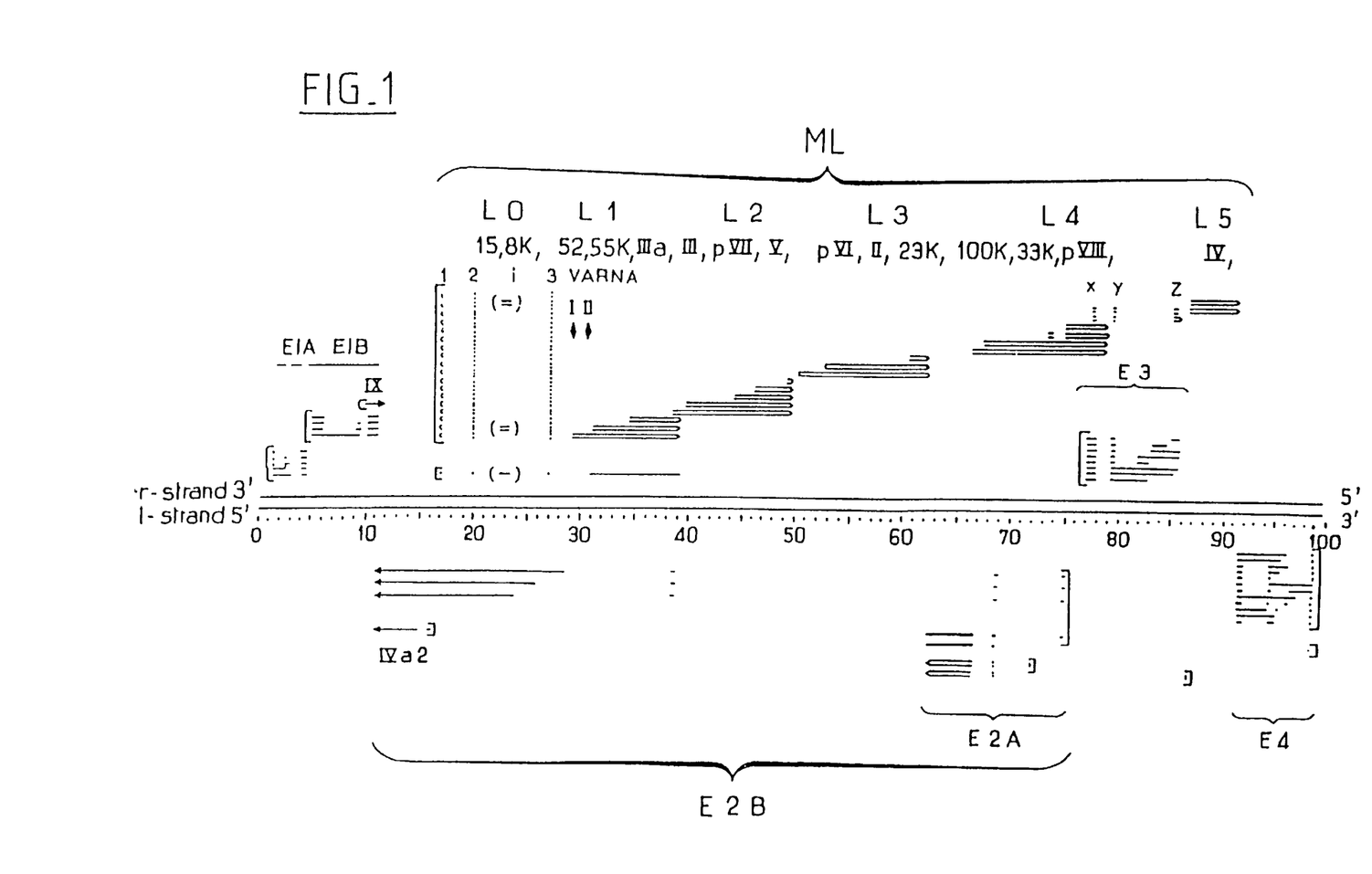
FIG. 1 is a schematic representation of the genome of the human adenovirus of type 5 (represented in arbitrary units from 0 to 100), indicating the position of the different genes.

The interest in adenoviruses as gene therapy vectors has already been touched on in numerous documents of the prior art. In fact, the adenoviruses have a wide spectrum of hosts, are not very pathogenic and do not have the disadvantages connected with the retroviruses since they are nonintegrative and replicate equally in quiescent cells. By way of information, their genome is formed of a linear and double-stranded DNA molecule of approximately 36 kb carrying regions acting in cis (ITR 5' and 5' encapsidation region of the viral genome and ITR 3') and additionally about thirty genes, at the same time early genes necessary for viral replication and late structure genes (see FIG. 1).

The early genes are divided into 4 regions dispersed in the adenoviral genome (E1 to E4; E for early). They comprise 6 transcriptional units which have their own promoters. The late genes (L1 to L5; L for late) partly cover the early transcription units and are, for the majority, transcribed starting from the major late promoter MLP.

At the present time, all the adenoviral vectors used in gene therapy protocols are devoid of the major part of the E1 region essential for replication, in order to avoid their distribution in the environment and the host organism (first generation vectors). This deletion makes the viral genome deficient for replication. However, the E1$^-$ viruses can be propagated in a cell line which complements the E1 function to generate an infectious viral particle. The 293 line, established starting from human embryonic kidney cells, is currently used, in the genome of which is integrated the left 5' end of the type 5 adenovirus (Graham et al., 1977, *J. Gen. Virol.* 36, 59–72).

The majority of adenoviral vectors of the prior art comprise supplementary deletions. Certain of these have been introduced in the E3 region with the aim of increasing the cloning capacities but do not need to be complemented to the extent where the E3 region is nonessential for replication. More recently, second generation vectors have been proposed in the literature. They conserve the in cis regions (ITRs and encapsidation sequences) and comprise important internal deletions aimed at suppressing the main part of the viral genes whose expression can be responsible for inflammatory responses in the host. In this respect, a minimal vector which is deficient for all of the coding viral regions represents a choice alternative.

The techniques of preparation of adenoviral vectors are widely described in the literature. Firstly, the complete genome is formed by homologous recombination in the 293 line (see especially Graham et Prevect, 1991, Methods in Molecular Biology, Vol. 7, Gene Transfer and Expression Protocols; Ed E. J. Murray, The Human Press Inc. Clinton, N.J.) or in *Escherichia coli* (technique described in the French Application No. 94 14470).

It is then necessary to propagate the vector in order to form a stock of viral particles containing it. This production step is critical and must allow high titers of infectious particles to be attained to be able to consider development on a large scale with a view to the preparation of clinical batches. If the first generation adenoviral vectors can be propagated relatively easily in the 293 cell line, the only complementation line described to date and capable of efficiently expressing E1, such is not the case for second generation vectors. In fact, according to the same basic principle, such a vector must be complemented for the essential functions which it cannot express.

The complementation can be provided "in trans" by the cell line employed (designated complementation cell line). It is then necessary to have new lines complementing several essential viral functions (E1 and E2, E1 and E4 or E1, E2 and E4) . However, the various attempts carried out until now give the impression that the coexpression of several adenoviral regions is potentially toxic, such that the line risks not being optimal in terms of growth capacity and yield of viral particles, these two criteria being indispensable for industrial exploitation.

Another alternative is based on the use of a supplementary viral element, called "helper virus" introduced into the line at the same time as the adeno-viral vector (two-component system). At the present time, an adenovirus from which the E1 region has been deleted and which is capable of synthesizing the expression products of other adenoviral regions is currently used. The co-transfection of such a helper virus and of an adenoviral vector in the 293 line allows the formation of viral particles.

However, a major disadvantage of this method is that the cells produce a mixed population of viral particles, one type comprising the recombinant vector and the other type the helper virus. In practice, the preparations mainly contain viral particles of helper virus, the contamination being able to reach and even exceed 90%. The presence of the helper virus is not desirable in the context of a therapy applied to man and therefore necessitates the employment of cumbersome and costly physical separation techniques, such as ultracentrifugation. In addition, this technology is not very well adapted to the production of vectors of complex structure, such as the second generation vectors, to the extent where, very often, the helper virus has a selective advantage (more rapid replication).

The unresolved problem to this day of the production of recombinant adenoviral vector particles with a high titer is an obstacle to the development of gene therapy.

A novel helper virus has now been constructed by insertion of direct repetitions on both sides of the encapsidation region. The action of a recombinase recognizing them involves the excision of the genetic material situated between them. This deletion does not have any notable consequence on the expression of the viral genes but limits the encapsidation of the helper virus in a viral particle. Thus, the employment of the two-component procedure described above in a cell line expressing thus recombinase will allow preparations enriched in adenoviral vector particles of interest to be produced.

The present invention follows from the perfection of a genetic technique based on the use of recombination sequences and of a recombinase to produce mainly the recombinant viral vector and to limit the contamination by the helper virus. The aim of the present invention is to put at the disposal of the public a novel helper virus able to express the genes which it carries (that is to say capable of exercising its function of transcomplementation) but unable to be propagated in the presence of a recombinase. The solution provided by the present invention combines safety of use (preparation enriched in recombinant viral vector), simplicity (production in a conventional cell line in the presence of recombinase) and efficiency (high titer compatible with industrial needs). It is very particularly adapted to the production of second generation adenoviral vectors.

For this reason the present invention relates to a helper virus for the production of a recombinant viral vector defective for replication, characterized in that it comprises a first recombination sequence at 5' and a second recombination sequence at 3' of a region essential for the propagation of said helper virus; said recombination sequences being recognized by a recombinase.

The term "helper virus" designates a vector able to trans-complement in full or in part a recombinant viral vector defective for replication. It is thus able to produce at least one polypeptide, early and/or late, which the recombinant vector cannot produce itself and which is necessary for the formation of a viral particle. "In full" signifies that the helper virus is capable of complementing the whole of the viral genome essential for replication of which the recombinant viral vector is devoid and "in part" signifies that the complementation is limited to a part of the defective functions.

In the context of the present invention, a helper virus derives from a natural virus such as found in nature as well as from a virus whose genome comprises modifications with respect to that of the parent virus from which it is descended. These modifications can have been introduced in vitro by genetic engineering techniques. They can be different (deletion, mutation and/or addition of one or more nucleotides) and localized in the encoding regions of the viral genome or outside of these. The modification can, for example, allow one or more gene(s) essential for viral replication to be inactivated with the aim of likewise rendering it defective that is to say incapable of autonomous replication.

The human adenoviruses of serotype C and, more particularly, of type 2, 5 or 7 represent particularly preferred viruses in the context of the invention. However, it is likewise possible to resort to other adenoviruses, especially of animal origin (canine, bovine, murine, avian, ovine, porcine or simian). It is, more particularly possible to mention the canine adenoviruses CAV-1 or CAV-2, avian viruses DAV or even bovine viruses Bad of type 3 (Zakharchuk et al., 1993, Arch. Virol., 128, 171–176; Spibey and Cavanagh, 1989, J. Gen. Virol., 70, 165–172; Jouvenne et al., 1987, Gene, 60, 21–28; Mittal et al., 1995, J. Gen. Virol., 76, 93–102). However, it may also be of interest to have a helper virus derived from a poxvirus (vaccinia virus, fowlpox, canarypox . . . ), retrovirus, herpesvirus, cytomegalovirus, adenovirus-associated virus (AAV) or even at a hybrid virus comprising fragments of different origin.

The characteristic of the helper virus according to the invention is that it comprises at least two recombination sequences inserted at 5' and at 3' of a sequence essential for its propagation. An essential sequence designates all or part of a viral gene, elements necessary for the expression such as a promoter or, in Et preferred manner, elements acting in cis (ITR, LTR, encapsidation sequence . . . ). By way of information, the first and/or second recombination sequences can be positioned in the interior or immediately at 5' and 3' of the essential region up to about several hundreds of bp.

In the sense of the present invention, a "recombination sequence" is formed by a nucleic acid sequence (DNA or RNA) recognized by a recombinase able to induce a recombination event. Usually, a recombination sequence has at least 10 base pairs (bp), advantageously 15 to 80 bp, preferably 20 to 60 bp and, in a very preferred manner, 30 to 50 bp. According to an advantageous embodiment, a helper virus according to the invention comprises two copies of an identical or closely similar recombination sequence (at least 70% sequence identity and, in a preferred manner at least 90%). For this reason we shall talk of sequence repetitions. In this respect, the repetition can be reversed (the two recombination sequences present in the helper virus have a reverse orientation with respect to one another, one being in the direction 5' to 3' and the other 3' to 5') or direct (same orientation 5' to 3' or 3' to 5'). This second form will be preferred.

The recombination is accompanied by a pairing of the recombination sequences, by a cleavage of a target sequence at their level and by a ligation of the cleaved ends. The enzyme able to promote the recombination is designated "recombinase". The recombination between direct repetitions leads to the excision of sequences between them. On the other hand, recombination between reversed repetitions involves the reversal of the genetic material located between them.

Generally speaking, the recombination sequences and the recombinases are described in the literature accessible to the person skilled in the art. They can be of any viral, phagic, prokaryotic or eukaryotic origin (yeast, fungus or even higher eukaryote). In addition, they can be obtained by the conventional molecular biology techniques (cloning, amplification by chain reaction (PCR for Polymerase Chain Reaction) or by chemical synthesis.

As preferred examples, mention will be made of loxP recombination sequences (described in the identifier of sequence SEQ ID NO.: 1), FRT (SEQ ID NO.: 2) and Ft (SEQ ID NO.: 3) recognized by the recombinases CRE, FLP and R, respectively (see, for example, the review article Kilby et al., 1993, TIG 9, 413–420).

A helper virus particularly adapted to the present invention is derived from the genome of an adenovirus and comprises the ITRs 5' and 3', an encapsidation region and at least one viral gene selected from the genes of the E1, E2, E4 and L1–L5 regions and defective in the recombinant adenoviral vector as well as al first recombination sequence at 5' and a second recombination sequence at 3' of the encapsidation region. Preferably, they are formed by loxP sequences positioned in the same orientation with respect to one another. According to a first variant of interest, the encapsidation region can be attenuated (reduced capacity for encapsidation) to favor the encapsidation of the recombinant viral vector. The attenuation can be obtained by deletion of a part of the encapsidation region. The means of attenuating an encapsidation region are indicated in the Application WO 94/28152.

According to a second variant of interest, the helper virus can include an expression cassette of a recombinase, and allowing especially an inducible expression or the production of an inactive recombinase activatable according to needs (defined below). The insertion takes place in an appropriate region of the helper virus and, preferably, outside of the localized region between the recombination sequences.

According to a particular embodiment intended to increase the safety aspect, a helper virus according to the invention can comprise a first recombination sequence and a second recombination sequence at 5' and at 3' of several regions essential to its propagation. For reasons of simplicity of employment, the case will be preferred where the recombination sequences are identical or related so as to be recognized by an identical recombinase.

The present invention likewise relates to a complementation cell line comprising a DNA fragment coding for a recombinase. It can be generated from various cell lines by introduction of appropriate portions of the viral genome and of the fragment in question. A line able to complement the E1 and/or E4 function of an adenovirus is more particularly preferred. Mention will be made of the lines 293 (Graham, 1997 supra) and 1653 (described in the Application WO 94/28152) modified by the introduction of the DNA fragment coding for a recombinase.

All the standard means for introducing a nucleic acid into a cell can be employed in the context of the present invention (synthetic, viral, plasmid vector, naked DNA . . . ). Of course, said DNA fragment can be integrated into the cell genome or remain in the episome state. For the aims of the present invention, it can comprise the elements necessary for its expression. These will be, preferably, elements conferring an inducible expression in response to an inducer. Such elements are known to the person skilled in the art. It is possible to mention, by way of information, promoters inducible by metals (promoter of the metallothioneine gene), by hormones (promoter comprising elements responding to glucocorticoids GRE, to progesterones PRE, to estrogens ERE . . . ), by viral inducers (promoter comprising the TRA or RRE sequence responding respectively to the TAT or REV protein of the human immunodeficiency virus HIV) or by various cellular inducers (promoter comprising the UAS-Gal4 sequence (for Upstream Activating Sequence Gal4) responding to Gal4 or the operators of the tetracycline bacterial operon responding positively to the transtetracycline activator tTA.

In addition, a DNA fragment in use in the present invention codes for a recombinase able to recognize the recombination sequences present in a helper virus according to the invention. It is preferred to employ a recombinase selected from the group formed by CRE, FLP and R. However, it is equally possible to resort to a DNA fragment coding for a homolog of a recombinase whose sequence is modified with respect to the native sequence but exercising a similar or improved function. These modifications can result from the deletion, addition or substitution of one or more nucleotide(s). They can likewise be a hybrid protein resulting from the fusion of polypeptides from various origins, especially a polypeptide having a recombinase activity and the other a linking region. A recombinase particularly adapted to the present invention is formed by a hybrid protein, designated CRE-ER, resulting from the fusion of the recombinase CRE and of the linking region to the ligand of the human estrogen receptor; (Metzger et al., 1995, Proc. Natl. Acad. Sci. USA 92). The latter insofar as such is inactive and its biological activity is activated in the presence of a hormonal ligand such as estradiol.

The invention likewise relates to a process for preparing a viral particle comprising a recombinant viral vector, which comprises the following steps:

(a) Preparing a recombinant viral vector deficient for replication;
(b) Preparing a helper virus according to the invention;
(c) Introducing the recombinant viral vector and the helper virus into an appropriate cell line;
(d) Culturing said cell line under appropriate conditions to allow the production of the viral particle in the presence of a functional recombinase able to recognize said first and second recombination sequences; and
(e) Recovering the viral particle in the cell culture.

In the sense of the present invention, a defective recombinant viral vector derives from a virus in the genome of which certain sequences have been deleted, rendered nonfunctional, mutated or even substituted by other sequences and, more particularly, a heterologous DNA fragment (normally not present in the parent virus). The insertion takes place in an appropriate region of the viral genome, so as to allow its expression in a host cell. A host cell is formed by any eukaryotic cell infectable by a viral particle containing said recombinant viral vector.

The heterologous DNA fragment in use in the present invention can be descended from a eukaryotic organism, from a prokaryote or from a virus other than that in which it is inserted. It can be isolated by any technique conventional in the field of the art, for example by cloning, PCR or chemical synthesis. It can be a fragment of genome type (comprising all or part of the whole of the introns), of complementary DNA type (cDNA, devoid of intron) or of mixed type (comprising all or part of at least one intron). In addition, it can code for an antisense RNA and/or a messenger RNA (mRNA) which will then be translated into a polypeptide of interest, the latter being able to be (i) intracellular, (ii) membranous present at the surface of the host cell or (iii) secreted into the external medium. In addition, it can be a polypeptide as found in nature (native) or a portion of the latter (truncated) or equally a chimeric polypeptide arising from the fusion of sequences of various origins or even mutated and having improved or modified biological properties.

In the context of the present invention, it can be advantageous to use a DNA fragment coding for a cytokine (interleukin including IL-2, interferon, colony-stimulating factor . . . ), a cell or nuclear receptor, a ligand, a clotting factor (factor VII, factor VIII, factor IX . . . ), CFTR protein (Cystic Fibrosis Transmembrane Conductance Regulator), insulin, dystrophin, a growth hormone, an enzyme (renin urease, thrombin . . . ), an enzyme inhibitor (inhibitor of a viral protease, alantitrypsin . . . ), a polypeptide with antitumor effect (product of suppressor genes of tumors, polypeptide stimulating the immune system . . . ), a polypeptide able to inhibit or slow down the development of a bacterial, viral or parasitic infection (antigenic polypeptide, trans-dominant variant . . . ), an antibody, a toxin, an immunotoxin and finally a label (luciferase, β-galactosidase, product conferring resistance to an antibiotic . . . ). Of course, this list is not limiting and other genes can likewise be employed.

Advantageously, the heterologous DNA fragment is placed under the control of elements necessary for its expression in the host cell. "Necessary elements" designates all of the elements allowing the transcription of said DNA fragment to RNA (antisense RNA or mRNA) and the translation of the mRNA to polypeptide. These elements comprise a regulatable or constitutive promoter, which can be heterologous or on the contrary homologous to the parent virus. It is possible to mention, as examples, the promoter of the human or murine PGK gene (Phospho Glycerate Kinase), the early promoter of the SV40 virus (Simian Virus), the LTR of RSV (Rous Sarcoma Virus), the TK promoter (Thymidine Kinase) of the HSV-1 virus (Herpes Simplex Virus) and the adenoviral promoters E1A and MLP. The necessary elements can, in addition, include additional elements (intron sequence, secretion signal sequence, nuclear localization sequence, translation initiation site, transcription termination poly A signal . . . ). Although it is not a preferred variant, it is indicated that the viral vector can likewise comprise a DNA fragment coding for the recombinase.

It is within reach of the person skilled in the art to generate a recombinant viral vector in use in the present invention. He will quite certainly know how to adapt the technology as a function of the specific data (type of vector, heterologous DNA fragment . . . ). According to a preferred variant, the vectors capable of being employed in the context of the present invention are recombinant adenoviral vectors defective for all of the viral functions or even all of the functions with the exception of E4. Such vectors are described in the International Application WO 94/28152.

A helper virus according to the invention is obtained by insertion in a viral genome of a first and a second recombination sequence on both sides of a region essential for replication and, preferably, of the encapsidation region, it being possible for the latter to be attenuated or nonattenuated. The person skilled in the art knows the regions essential for the replication of a virus and is able to carry out such a construction by applying the classical techniques of molecular biology. According to the variant mentioned above, it can likewise comprise a DNA fragment coding for a recombinase and, especially, the CRE-ER hybrid. According to a preferential embodiment, a helper virus according to the invention and the recombinant viral vector which it allows production of derive from the same parent virus and, in a very preferred manner, from an adenovirus.

After the actual construction step, the helper virus and the recombinant viral vector are introduced into an appropriate cell line. All the standard means for introducing a nucleic acid into a cell can be used in the context of the present invention, for example transfection, electroporation, microinjection, lipofection, adsorption and fusion of protoplasts. It is indicated that they can be co-introduced (concomitant fashion) or introduced separately (the helper virus according to the invention previously or subsequently to the recombinant viral vector).

Although any cell line can be employed in the context of the present invention, a complementation line is especially preferred. Recourse will be had to a line of the prior art (293, 1653 . . . ) when a recombinant viral vector or a helper virus comprising the DNA fragment coding for the recombinase is employed. On the other hand, when this is not the case, use will be made of a complementation cell line according to the invention.

After transfection, the cell line is cultured under appropriate conditions to allow the production of viral particles. A procedure according to the invention can, in addition, comprise an amplification step previous to the culture step in the presence of the functional recombinase. The aim of this step is to increase the quantities of helper virus and of recombinant viral vector in order to improve the yields. It can be carried out by culture in any permissive line or in the appropriate line in use in the present invention before the addition, expression or activation of the recombinase.

This first culture step is followed by a second step carried out in the presence of a functional recombinase able to recognize said first and second recombination sequences. In the context of the procedure according to the invention, this recombinase can be added to the cell culture, for example in substantially pure form. However, according to another very preferred and already mentioned variant, the recombinase is produced by one of the constituents of the procedure according to the invention, namely the recombinant viral vector or, in a preferred manner, the helper virus or the cell line. Once produced in functional form, the recombinase will cause the excision of the essential region of the helper virus localized between the recombination sequences, with the aim of preventing or reducing its propagation.

In addition, when a recombinase is employed whose expression is inducible by an inducer or the CRE-ER hybrid protein whose biological activity is dependent on a hormonal ligand, the culture step in the presence of the functional recombinase is carried out by the addition to the culture medium of the inducer or the ligand.

According to an advantageous embodiment intended to increase the safety of a procedure according to the invention, the helper virus and the recombinant viral vector are defective and can be conversely complemented, in total or in part. A variant of interest consists in employing (i) a helper adenovirus according to the invention defective for the functions E1 and E4 and comprising the loxP sequences at 5' and at 3' of the encapsidation region, (attenuated or nonattenuated) (ii) a recombinant vector defective for all the functions with the exception of E4 and (iii) a 293 cell line producing the CRE-ER hybrid recombinase. According to another advantageous alternative, a procedure according to the invention employs (i) a helper adenovirus according to the invention defective for the functions E1 and E4, comprising the loxP sequences at 5' and at 3' of the encapsidation region (attenuated or nonattenuated) and producing the CRE-ER hybrid recombinase, (ii) a recombinant vector defective for all of the functions with the exception of E4 and (iii) a conventional cell line 293.

The viral particles are recovered from the cell culture, from the medium or after lysis of the cells. Advantageously, a procedure according to the invention comprises an additional step of purification of the recombinant viral vector particles. Although the choice of the technique is wide and within the reach of the person skilled in the art, it is possible to mention more particularly ultracentrifugation on a cesium chloride or sucrose gradient.

Finally, the invention likewise relates to a procedure for preparing a viral particle comprising a recombinant viral vector by means of a helper virus, according to which the ratio viral particles of recombinant adenoviral vector to those of helper virus is greater than 50%, advantageously greater than 60%, preferably greater than 70% and, in a very preferred manner, greater than 80%.

The invention likewise relates to a recombinant viral vector particle obtained by a procedure according to the invention as well as to a eukaryotic host cell according to the invention. Said host cell is advantageously a mammalian cell and, preferably, a human cell and can comprise said vector in integrated form in the genome or in nonintegrated form (episome). It can be a primary or tumor cell of hematopoietic (totipotent stem cell, leukocyte, lymphocyte, monocyte or macrophage . . . ), muscular, pulmonary, tracheal, hepatic, epithelial or fibroblast origin.

The invention likewise relates to a pharmaceutical composition comprising as therapeutic or prophylactic agent a recombinant viral vector particle obtained by a procedure according to the invention or a eukaryotic host cell according to the invention, in combination with a carrier acceptable from a pharmaceutical point of view. The composition according to the invention is intended in particular for the preventive or curative treatment of diseases such as:

genetic diseases (hemophilia, mucoviscidosis, diabetes or myopathy, that of Duchene and Becker . . . ), cancers, such as those induced by oncogenes or viruses, viral diseases, such as hepatitis B or C or AIDS (acquired immunodeficiency syndrome resulting from infection by HIV), and recurrent viral diseases, such as viral infections caused by the herpesvirus.

A pharmaceutical composition according to the invention can be produced in a conventional manner. In particular, a therapeutically efficacious quantity of a therapeutic or prophylactic agent is combined with a carrier such as a diluent. A composition according to the invention can be administered by aerosol, locally or even systemically. The routes of administration envisagable within the context of the present invention can be intragastric, subcutaneous, intracardiac, intramuscular, intravenous, intraperitoneal, intratumor, intrapulmonary, nasal or intratracheal. The administration can take place in a single or repeated dose one or more times after a certain delay interval. The appropriate route of administration and the appropriate dose vary as a function of various parameters, for example of the individual or of the disease to be treated or even of the recombinant gene(s) to be transferred. In particular, the viral particles according to the invention can be formulated in the form of doses of between $10^4$ and $10^{14}$ pfu (plaque-forming units), advantageously $10^5$ and $10^{13}$ pfu and, preferably, $10^6$ and $10^{11}$ pfu. The formulation can likewise include an adjuvant which is acceptable from a pharmaceutical point of view.

Finally, the present invention relates to the therapeutic or prophylactic use of a recombinant viral vector particle obtained by a procedure according to the invention or of a eukaryotic host cell according to the invention for the preparation of a medicament intended for the treatment of the human or animal body and, preferentially, by gene therapy. According to a first possibility, the medicament can be administered directly in vivo (for example in an accessible tumor, in the lungs by aerosol . . . ). It is likewise possible to adopt the ex vivo approach which consists in taking cells from the patient (stem cells of the bone marrow, peripheral blood lymphocytes, muscle cells . . . ), in transfecting or infecting them in vitro according to the techniques of the art and in readministering them to the patient.

The invention likewise extends to a method of treatment according to which a therapeutically efficacious quantity of a recombinant viral vector particle obtained by a procedure according to the invention or of a eukaryotic host cell according to the invention is administered to a patient having need of such a treatment.

The present invention is described more completely with reference to the following figures and with the aid of the following examples.

EXAMPLES

The following examples only illustrate one method of carrying out the present invention.

The constructs described below are carried out according to the general techniques of gene therapy and of molecular cloning, detailed in Maniatis et al., (1989, Laboratory Manual, Cold Spring Harbor, Laboratory Press, Cold Spring Harbor, N.Y.) or according to the recommendations of the manufacturer when using a commercial kit.

The cloning steps employing bacterial plasmids are carried out in the strain Escherichia coli (E. coli) 5K (Hubacek and Glover, 1970, J. Mol. Biol. 50, 111–127) or BJ5183 (Hanahan, 1983, J. Mol. Biol. 166, 557–580). This latter strain is preferentially used for the homologous recombination steps. The techniques of amplification by PCR are known to the person skilled in the art (see, for example, PCR Protocols—A guide to methods and applications, 1990, edited by Innis, Gelfand, Sninsky and White, Academic Press Inc.). Being a question of the repair of restriction sites, the technique employed consists in filling the protruding 5' ends with the aid of the large fragment of DNA polymerase I from E. coli (Klenow).

As far as the cellular biology is concerned, the cells are transfected according to the standard techniques well known to the person skilled in the art. The calcium phosphate technique can be mentioned (Maniatis et al., supra), but any other protocol can likewise be employed, such as the DEAE dextran technique, electroporation, methods based on osmotic shock, microinjection of a selected cell or methods based on the use of liposomes. As for the culture conditions, they are conventional except when specified.

In the examples which follow, recourse is had to the following cell lines:

Line 293 derived from embryonic human kidney (Graham et al., 1977, supra) which results from the integration into its chromosomes of the 5' end of the genome of Ad5 (ITR5', encapsidation sequence and E1 region) (available at the ATCC under reference 1573).

Line TG1653 (described in the International Application WO94/28152, Example 8) which derives from the line 293 transformed in a stable manner by the plasmid pTG1653 carrying the E4 region of Ad5 (nt 32800 to 35826) and the expression cassette of the pac (Puromycin Acetyl Transferase) puromycin resistance gene (Morgenstern and Land, 1990, Nucleic Acids Res. 18, 3587–3596).

It is understood that other cell lines can be used.

In addition, the fragments of adenoviral genome employed in the different constructs described below are indicated precisely according to their positions in the nucleotide sequence of the genome of AdS such as disclosed in the Genebank databank under the reference M73260.

Example 1

Formation of a helper virus.

This example describes the construction of an adenoviral helper virus defective for the functions E1 and E4 and comprising an loxP recombination sequence positioned on both sides of the encapsidation region.

The loxP sequence is carried by the oligonucleotides oTG6374 and oTG6522 (SEQ ID NO: 4 and 5). These are reassociated and then introduced into the HindIII site of the p poly II vector (Lathe et al., Gene 57, 193–201) to give pTG4691.

Figure 2:
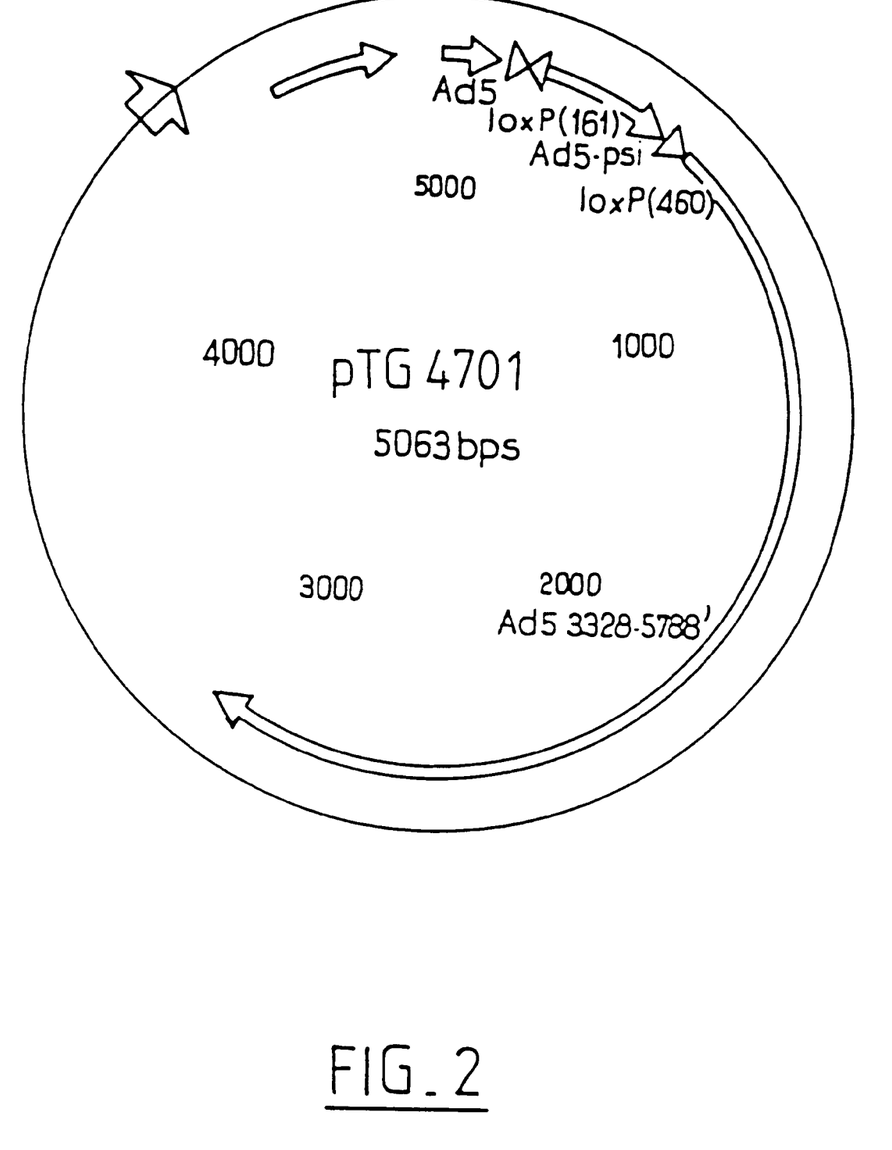
FIG. 2 is a schematic representation of the pTG4701 vector in which the left 5' region of the 5 adenovirus is modified by the insertion of LoxP direct repetitions on both sides (in positions 161 and 460) of the encapsidation region (psi).

The vector pTG8343 arises from the insertion in the p poly II vector of a part of the 5' end of the adenoviral genome, namely the sequences extending from the nucleotides (nt) 1 to 458 and 3328 to 5788. This is linearized by SalI and ligated with the SalI-XhoI fragment isolated from pTG4691 carrying the loxP sequence. pTG4695 is obtained, which comprises an loxP sequence in position 450 of the adenoviral genome or at 3' of the encapsidation region. A second loxP sequence is cloned in the form of a SmaI-PvuII fragment purified of pTG4691 in the preceding vector linearized by AflIII (position 161) and treated with Klenow. The pTG4701 vector thus obtained comprises two direct loxP repetitions surrounding the psi encapsidation region (FIG. 2).

Figure 3:
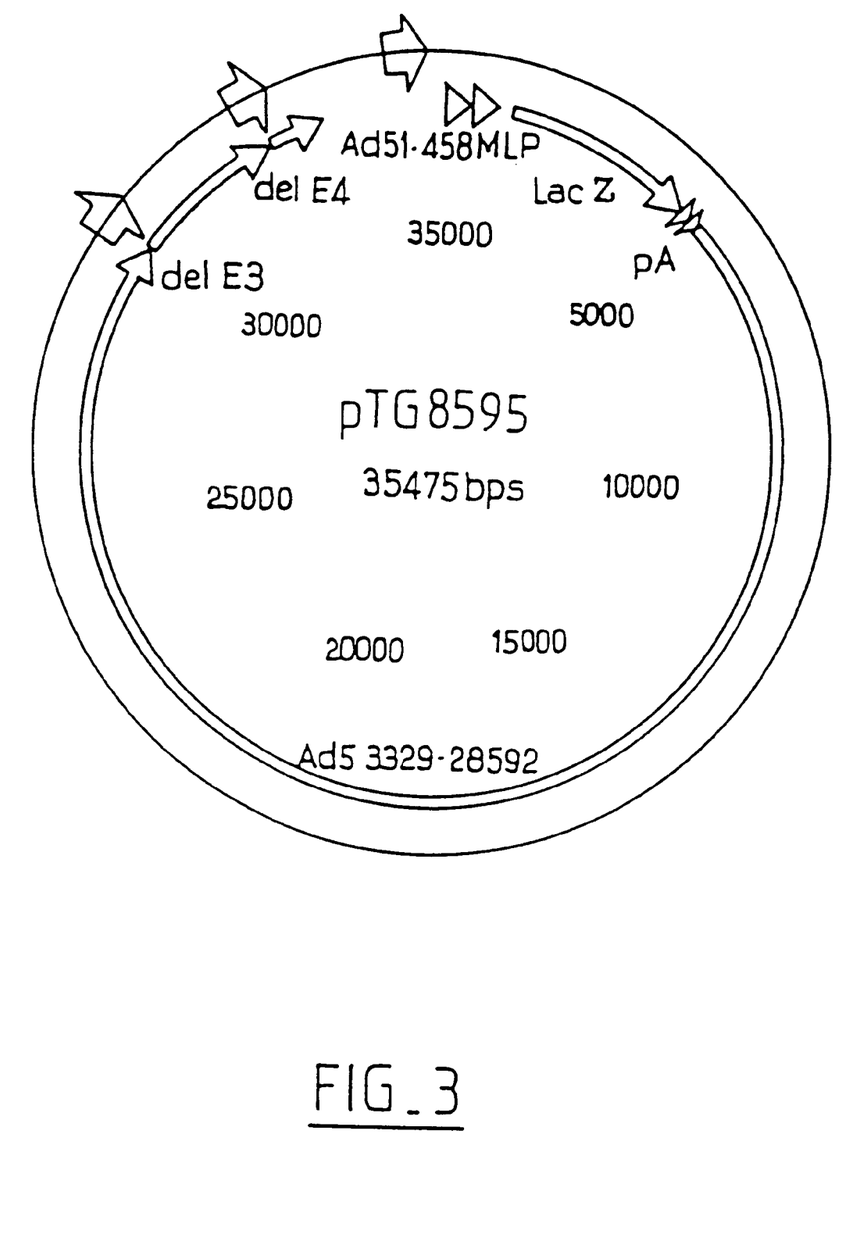
FIG. 3 is a schematic representation of the pTG8595 vector with the E1, E3 and E4 regions and comprising an expression cassette of the LacZ gene controlled by the MLP promoter and a polyA sequence (pA).
Figure 4:
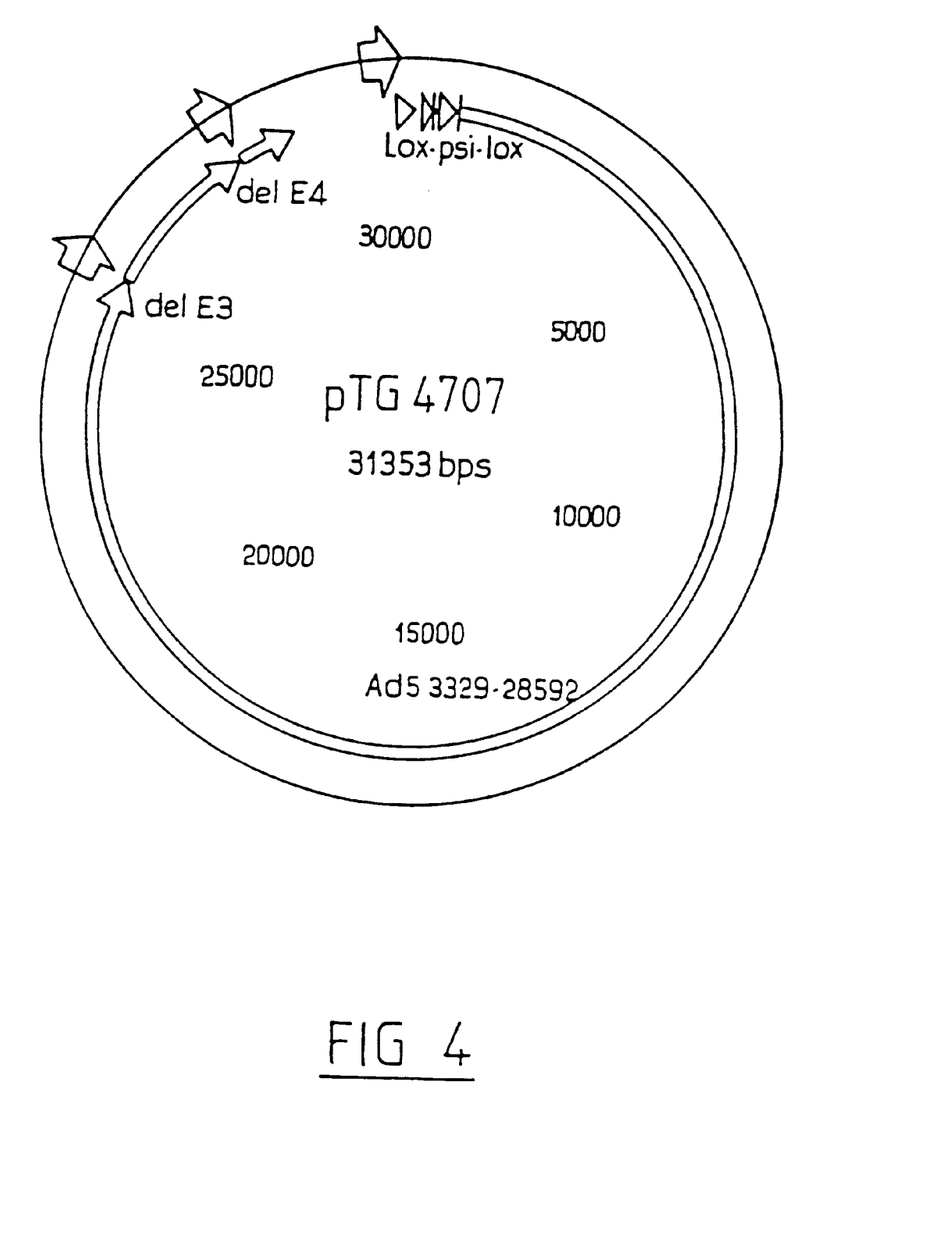
FIG. 4 is a schematic representation of the pTG4707 vector with the E1, E3 and E4 regions and comprising two LoxP direct repetitions on both sides of the psi encapsidation region.

The modified encapsidation region is exchanged for its genomic homolog by the technique of homologous recombination. To this end, the E. coli strain is co-transformed with the BglI fragment of pTG4701 and the pTG8595 vector (FIG. 3) digested by ClaI. The latter is a recombinant adenoviral vector with the E1 (nt 459–3328), E3 (nt 28592–30470) and E4 (nt 32800–35826) regions deleted and comprising an expression cassette of the LacZ gene under the control of the MLP promoter in place of the E1 region. The recombined vector is designated pTG4707 (FIG. 4). After transfection in the TG1653 complementation line ($E^{1+}$, $E^{4+}$) and amplification, the Ad TG4707 viruses are purified on a cesium chloride gradient so as to form a viral stock titrating approximately $2 \times 10^8$ pfu/ml.

Example 2

Construction of a recombinant adenoviral vector producing a recombinase.

This example describes the construction of an adenoviral vector expressing the CRE-ER hybrid protein. In the absence of estrogen, the latter is produced in an inactive form but in the presence of the hormone, it adopts an active conformation. The adenoviral vector is devoid of most of the E1 and E3 regions and of the part of the E4 region other than the ORFs 6 and 7 (Open Reading Frame). The expression of these two genes is sufficient to assure the E4 function without necessity for complementation (Ketner et al., 1989, Nucleic Acids Res. 17, 3037–3048). Two types of vectors have been constructed. In the first (pTG4708), the CRE-ER gene is placed under the control of the SV40 promoter although in the second (pTG5630), it is directed by the CMV promoter.

Figure 5:
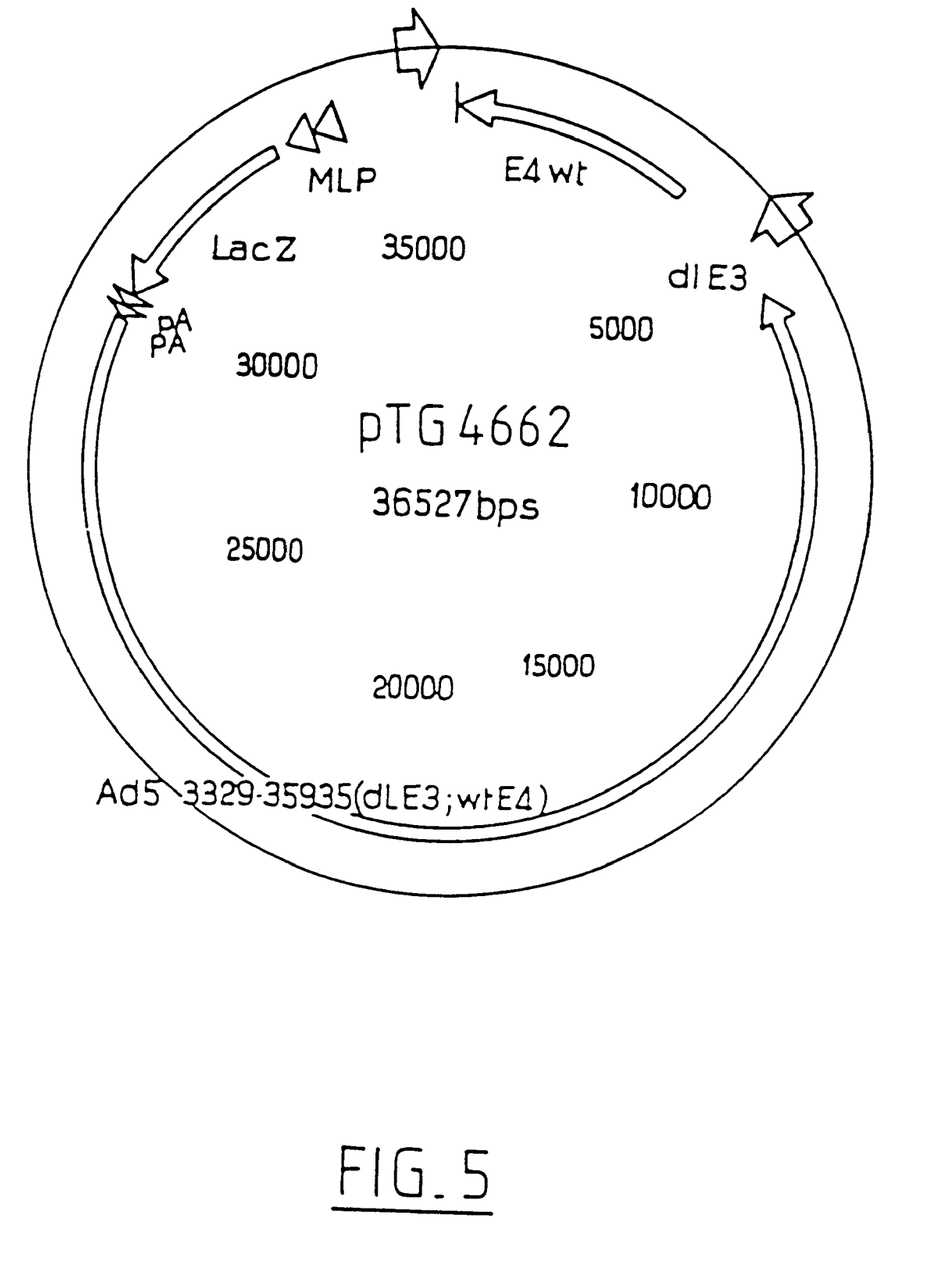
FIG. 5 is a schematic representation of the pTG4662 vector, a recombinant adenoviral vector with the E1 and E3 regions and carrying the same LacZ cassette as pTG8595.
Figure 6:
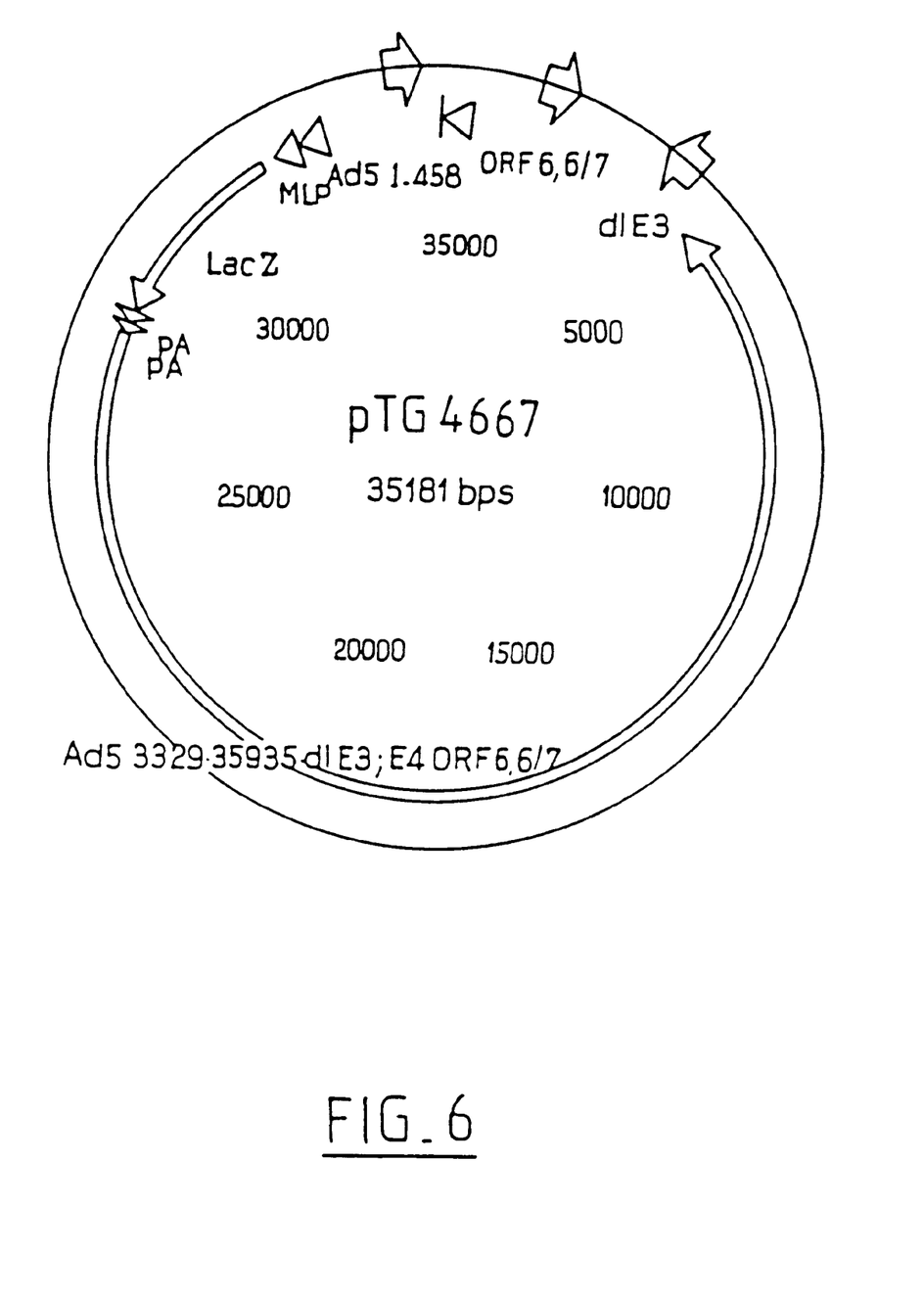
FIG. 6 is a schematic representation of the vector pTG4667, a recombinant adenoviral vector with the E1, E3 regions and the ORFs 1 to 4 of E4 deleted and carrying the same LacZ cassette as pTG8595.

In the first place, the pTG1653 vector carrying the E4 region of Ad5 (nt 32800 to 35826; see WO 94/28152), is digested by AvrII and BglII and then treated by Klenow before being religated on itself. pTG4660 which carries an expression cassette of the ORFs 6 and 7 under the control of the homologous promoter E4 is obtained. This is introduced into an adenoviral vector by homologous recombination. To this end, the vector pTG4662 (FIG. 5) is chosen which comprises the ITR 5' and the encapsidation sequences (nt 1 to 458), an expression cassette of the LacZ gene in the place of the E1 region and the remaining adenoviral sequences with the E3 region (nt 3329 to 27870 and 30749 to 35935) deleted. The E. coli BJ strain is co-transformed by the FspI-MunI fragment descended from pTG4660 and pTG4662 digested by SwaI. This recombination event allows pTG4667 (FIG. 6) to be generated, in which the cassette ORFs 6 and 7 replace the E4 wild region.

A. Construction of the pTG4708 vector

In parallel, the expression cassette of the CRE-ER hybrid recombinase is isolated from the pCre-ER vector (Metzger et al., 1995, supra) in the form of a SalI fragment and cloned in the vector pTG8343 previously linearized by this same enzyme. pTG4699 and pTG4700 which differ by the orientation of the cassette are obtained.

Figure 7:
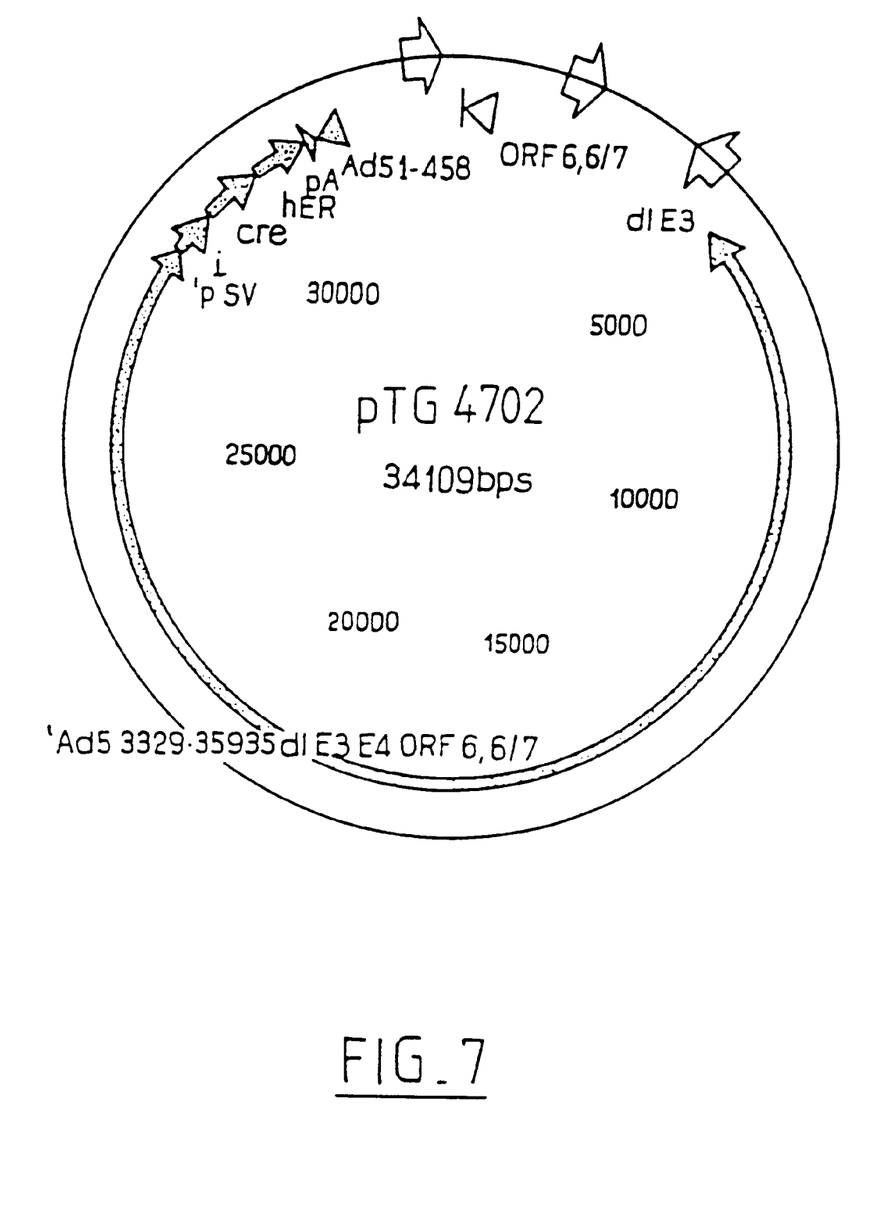
FIG. 7 is a schematic representation of the pTG4702 vector which derives from the above vector by insertion of an expression cassette of the CRE-ER hybrid protein (indicated cre and hER) in place of that of LacZ.

The vectors pTG4702 (FIG. 7) and pTG4703 are obtained by homologous recombination between a purified SgrAI-BstEII fragment of pTG4699 and pTG4700 respectively and the adenoviral vector pTG4667 linearized by ClaI. They carry the CRE-ER expression cassette (different orientation for each of them) in place of the E1 region and are devoid of the E3 region and of the ORFs 1 to 4 of E4. They are transfected in the 293 and 1653 cells so as to ensure that the expression of the recombinase is not toxic to cell growth and to viral multiplication.

The construction of an adenoviral vector, in addition, defective for the E2 region can be carried out starting from previous constructs by treatment with the AscI enzyme and religation. The clones are isolated which have reintegrated the AscI fragment but in opposite orientation with respect to the parent vector. The candidates can be determined by simple enzymatic digestion with enzymes whose sites are present on the fragment, for example BamHI and are designated pTG4708. The aim of this reversal of the orientation is to interrupt the transcription units coding for E2A, the polymerase and the hexon and to render the E2 function defective. It is equally possible to introduce deletions of all or part of the E2 region.

B. Construction of the pTG5630 vector

The vector pTG4667 is digested by the SnaBI enzyme and then religated. The vector pTG5613 similar to pTG4667 is selected except for the reversal of the adenoviral fragment SnaBI (positions 10307 to 25173) covering a large part of the coding sequences of the E2 region. This reversal allows a defective virus to be generated which is incapable of producing the functional expression products of E2.

In addition, the sequences coding for CRE-ER are isolated by EcoRI digestion and treated by Klenow before being introduced upstream of the CMV promoter, giving rise to pTG5625. The vector pTG5630 is obtained by homologous recombination between the PacI-BstEII fragment isolated from pTG5625 and the vector pTG5617 linearized by ClaI. pTG5630 is defective for the E1 and E2 functions, with the major part of E3 deleted, and carries the "CMV—CRE-ER promoter" cassette in place of E1 in reverse orientation with respect to the 5' ITR.

Example 3

Procedure for preparation of viral particles of an adenoviral vector by the system CRE and loxP.

A. Employment of the vector pTG4708 and the helper pTG4707

In this example, the following are used:
(1) an adenoviral vector (pTG4708) defective for all of the adenoviral functions with the exception of E4 and carrying the sequences coding for the recombinase CRE-ER,
(2) a helper virus (pTG4707) defective for the functions E1, E3 and E4 and containing two loxP direct repetitions placed on both sides of the encapsidation region, and
(3) the 293 complementation cell line complementing the E1 function.

The vectors pTG4707 and pTG4708 are co-transfected in 293 cells and cultured at first in a conventional medium not containing estrogen. The viral particles can be formed in the cells which comprise the two vectors since they are mutually complementary. In fact, the E2 proteins are produced from the helper virus, the E4 proteins from the adenoviral vector and the E1 proteins are supplied by the cell line. In addition, the CRE-ER hybrid protein is produced in its inactive form since the culture medium is not supplemented by hormone such that the genome of the helper virus is able to be encapsidated. The plaques thus produced contain a mixed population of virus, one part containing the genome of the adenoviral vector and the other part that of the helper virus. This step allows an amplification of the quantity of virus with the aim of improving the titers.

The step of selective production of the particles of adenoviral vector is carried out by introducing into the culture medium estradiol according to the conditions detailed in Metzger et al. (1995, supra). The presence of estradiol will allow the CRE-ER recombinase to be activated which, once functional, is able to induce a recombination event between the loxP sequences. The viruses generated under these conditions are purified, the DNA is isolated and the deletion of the encapsidation region verified either by enzymatic digestion or hybridization with an appropriate probe complementary to that according to the technology of Southern.

B. Employment of the vector pTGS630 and of the helper pTG4707

2.5 to 5 $\mu$g of pTG5630 vector are transfected in the 293 line under the conventional conditions. The following day the transfected cells are superinfected by the helper virus AdTG4707 at a rate of approximately 0.04 pfu/cell and cultured in a DMEM medium depleted of Phenol Red (the latter being capable of having an estrogenic activity). Two conditions for culture were studied in parallel: medium supplemented by $\gamma$-estradiol (Sigma; E4389) at a concentration of $10^{-6}$ and $10^{-7}$M after the third passage and nonsupplemented medium. The cell culture is harvested at 4 days post-infection and a part of the harvest amplified by successive passages over fresh 293 cells. The other part is preserved for the viral DNA analyses. A significant difference is observed in the state of the cells according to the culture conditions. In fact, the cytopathy is less pronounced in the presence of estradiol than in its absence, this counting from the third passage, which allows a difference to be shown at the level of viral production.

In order to verify this point, the DNA of the viruses produced during the four first passages is isolated from an identical volume of culture, digested by the enzyme MunI and analyzed by Southern with the aid of a radioactive probe complementary to a sequence upstream of the E4 region. After hybridization, an MunI fragment of 1.7 kb is visualized in the case of the viruses descended from the pTG5630 vector and a MunI fragment of 1.1 kb in the case of the AdTG4707 helper viruses. These conditions allow the relative quantity of virus of interest and helpers generated in each amplification cycle to be seen.

Under the conditions where the CRE-ER recombinase is inactive (in the absence of estrogen), a simultaneous amplification of the two types of virus is observed showing itself by a more and more intense signal in proportion to the passages. On the other hand, when the culture medium is supplemented by estradiol, the signal corresponding to the helper virus decreases although that specific for AdTG5630 increases with each passage. These results indicate that the activation of the recombinase is accompanied by a preferential amplification of the virus of interest.

The excision of the encapsidation region of the helper virus is demonstrated by Southern analysis on the viral DNA preparations digested by the enzyme AflII and employing a specific probe of the encapsidation region hybridizing to a fragment of 3.7 kb in the case of the AdTG5630 virus and to a fragment of either 800 bp in the case of the complete helper virus or 400 bp in the case where the encapsidation sequences bordered by the loxP sites are excised.

The intensity of the signal corresponding to the fragment of 3.7 kb increases in proportion to amplification cycles whatever the culture conditions although that corresponding to the 800 bp fragment only increases in the absence of estradiol. On the other hand, in the presence of the hormone, the signal corresponding to the helper virus grows weaker. With high exposure, it is possible to demonstrate a band at 400 pb indicating that the encapsidation region of the helper viruses is excised by the action of the recombinase.

In their entirety, these results show that the CRE-LoxP system can be adapted to the adenoviruses to reduce the contamination of the adenoviral preparations by the helper virus.

Example 4

Formation of a stable line expressing the CRE-ER hybrid recombinase.

The pCre-ER vector is transfected, in a conventional manner, in the 293 cells at the same as a selection vector (for example pRC-CMV conferring resistance to commercially available neomycin (Invitrogen), pTG1643 conferring resistance to puromycin described in WO 94/28156). After transfection, the cells are cultured in selective medium containing the antibiotic and the resistant clones (designated 293/CRE-ER) are isolated and are tested for their capacity to produce an adenoviral vector.

The same technology is used to generate a 1653 line (complementing the adenoviral functions E1 and E4) expressing the CRE-ER gene product.

The 293/CRE-ER cells thus generated are co-transfected by the pTG4707 helper virus and a recombinant adenoviral vector defective for all the functions with the exception of E4 (such as those described in WO 94/28152) and then cultured in a conventional medium so as to generate a mixed and amplified population of viral particles. After a certain time, the culture medium is replaced by a medium containing estradiol in order to produce the recombinase in its active form and to prevent the production of AdTG4707 viral particles.

The 1653/CRE-ER line will be useful for the preparation of vectors defective for all of the essential functions (see WO 94/28156). The technology employed is comparable to that described above, namely: co-transfection by the pTG4707 helper virus and a minimum recombinant adenoviral vector, culture in selective medium which is not supplemented by estradiol for a sufficient time and then addition of the hormone to the culture medium and recovery of the viral particles produced.

What is claimed is:

1. A DNA fragment encoding a recombinase able to recognize a recombination sequence wherein said recombinase is a hybrid protein resulting from the fusion of a polypeptide sequence having a recombinase activity with a linking region which can be recognized by a ligand.

2. The DNA fragment of claim 1, wherein said recombinase is inactive in the absence of said ligand.

3. The DNA fragment of claim 1, wherein said polypeptide sequence having a recombinase activity is CRE.

4. A cell line complementing a replication defective adenoviral vector and comprising the DNA fragment of claim 1.

5. A helper virus, which complements in trans a recombinant adenoviral vector defective for replication comprising a first recombination sequence 5' and a second recombination sequence 3' of a region essential to the propagation of said helper virus, wherein said recombination sequences are recognized by a recombinase, and wherein said helper virus further comprises the DNA fragment of claim 1.

6. The DNA fragment of claim 3, wherein said linking region is the linking region of the human estrogen ER.

7. The complementation cell line of claim 4, wherein the DNA fragment is able to complement an E1 and/or E4 function of said adenoviral vector defective for replication.

8. The complementation cell line of claim 4, wherein the recombinase is the group consisting of CRE-ER, FLP and R.

9. The complementation cell line of claim 7, wherein the cell line is a 293 cell line.

10. The helper virus of claim 5, wherein the helper virus is deficient for replication.

11. The helper virus of claim 5, wherein said recombination sequences are positioned 5' and 3' of the encapsidation region of said helper virus.

12. The helper virus of claim 5, wherein said first and second recombination sequences are in the same orientation.

13. The helper virus of claim 5, wherein said first and second recombination sequences are selected from the group consisting of loxP, FRT and R.

14. The helper virus of claim 5 for producing a recombinant adenoviral vector defective for replication, said helper virus further comprising: (i) ITRs 5' and 3', an encapsidation region and at least one viral gene selected from the group consisting of E1, E2, E4 and L1–L5 regions from an adenovirus genome, and (ii) a first recombination sequence 5' and a second recombination sequence 3' of said encapsidation region.

15. A process for preparing an adenoviral particle comprising a recombinant adenoviral vector, which comprises the following steps:
   (i) preparing a recombinant adenoviral vector deficient for replication;
   (ii) preparing a helper virus according to claim 5;
   (iii) introducing the recombinant adenoviral vector and the helper virus into an appropriate cell line;
   (iv) culturing said cell line under appropriate conditions to allow the production of the viral particle in the presence of a recombinase able to recognize said first and second recombination sequences, wherein in the course of step (iv), the ligand of the linking region is added; and
   (v) recovering the adenoviral particle in the cell culture.

16. The helper virus of claim 5, wherein the helper virus is an adenovirus.

17. The helper virus of claim 13, wherein the loxP sequence is SEQ ID NO.:1.

18. A helper virus of claim 13, wherein the FRT sequence is SEQ ID NO.:2.

19. A helper virus of claim 13, wherein the R sequence is SEQ ID NO.:3.

20. The helper virus of claim 14, wherein said helper virus is devoid of all or part of E1 and/or E4 regions.

21. The process of claim 15, wherein said recombinase is a hybrid recombinase CRE-ER, said first and second recombination sequences are lox sequences and said ligand is estradiol.

22. The helper virus of claim 16, wherein the adenovirus is a human, canine, murine, bovine, avian, ovine simian or porcine adenovirus.

23. The helper virus of claim 16, wherein the adenovirus is CAV-1, CAV-2, avian viruses DAV, or bovine viruses Bad of type 3.

24. The helper virus of claim 22, wherein the human adenovirus is of serotype C and is selected from the group consisting of type 2, type 5 and type 7.

* * * * *